US011943218B2

(12) United States Patent
Chavakula

(10) Patent No.: US 11,943,218 B2
(45) Date of Patent: Mar. 26, 2024

(54) AUTOMATED OPERATING SYSTEM

(71) Applicant: Anand Kumar Chavakula, Hyattsville, MD (US)

(72) Inventor: Anand Kumar Chavakula, Hyattsville, MD (US)

( * ) Notice: Subject to any disclaimer, the term of this patent is extended or adjusted under 35 U.S.C. 154(b) by 708 days.

(21) Appl. No.: 17/090,545

(22) Filed: Nov. 5, 2020

(65) Prior Publication Data

US 2021/0051145 A1   Feb. 18, 2021

Related U.S. Application Data

(63) Continuation-in-part of application No. 16/287,066, filed on Feb. 27, 2019, now Pat. No. 10,856,782.

(60) Provisional application No. 62/917,619, filed on Dec. 19, 2018.

(51) Int. Cl.
*G06F 21/00* (2013.01)
*G06F 16/9035* (2019.01)
*H04L 9/40* (2022.01)

(52) U.S. Cl.
CPC ...... *H04L 63/0861* (2013.01); *G06F 16/9035* (2019.01); *H04L 63/083* (2013.01)

(58) Field of Classification Search
None
See application file for complete search history.

(56) References Cited

U.S. PATENT DOCUMENTS

| 10,856,782 | B2* | 12/2020 | Chavakula | A61B 5/150358 |
| 2007/0250920 | A1* | 10/2007 | Lindsay | G06F 21/31 726/7 |
| 2011/0083016 | A1* | 4/2011 | Kesanupalli | G06Q 20/40 713/180 |
| 2014/0195815 | A1* | 7/2014 | Taveau | G06F 21/32 713/186 |
| 2018/0165508 | A1* | 6/2018 | Othman | G06F 21/32 |
| 2021/0051145 | A1* | 2/2021 | Chavakula | A61B 5/150022 |
| 2021/0344662 | A1* | 11/2021 | Miu | G06Q 20/4016 |

* cited by examiner

*Primary Examiner* — Jeffery L Williams

(57) ABSTRACT

An automated computer operating software system for automatically generating user profiles is disclosed. The system is configured to automatically creates a profile or a number profiles based on biometric methods but also stores the profile(s) information along with an associated device(s) information and user generated data locally and remotely through various hardware modules and can also retrieve this information to any other device based on biometric authentication on the other device and auto adjust the operating parameters according to that other device and its operational parameters and again continue this same kind of auto creating, backing up and retrieving of both the profile of the user and device as well in a continuous loop of infinite number devices and user profiles.

10 Claims, 13 Drawing Sheets

AUTOMATED OPERATING SYSTEM

CROSS-REFERENCE TO RELATED APPLICATIONS

This application is a Continuation in Parts application of U.S. patent application Ser. No. 16/287,066 filed Feb. 27, 2019, which claims the priority benefit OF U.S. provisional patent application Ser. No. 62/917,619 filed on Dec. 19, 2018, the entirety of which is incorporated herein by reference for all purposes.

BACKGROUND OF THE INNOVATION

A. Technical Field

The invention disclosed herein generally relates to a computer software operating system that can be used to operate hardware and installed software or application systems on board a computer's hardware in a way that is highly automated based on any number of biometric detecting sensors that are integrated on the hardware portion of the computer. More particularly, the present invention relates to a computer software system operated by a combination of built-in biometric sensors, memory modules, a hardware storage medium, a computer networking system, related modules, and peripherals that are powered by AC or DC electrical power to automatically enable the creation of at least one or more individual profiles based on onboard multiple methods of biometric sensors.

B. Description of Related Art

Software operating systems and related computer applications are used on a variety of computer hardware systems to be able to conduct many diverse functions to aid in many types of user defined purposes in the fields of science, finance, health, entertainment, social media, data storage, calculations and such to accomplish various tasks with great efficiency. Many software systems that aid in carrying out user defined functions on various hardware systems first require a certain amount of customization and personalization by a manual creation of an account by a user to be able to create and store various user generated information. Once a personal account is manually created either on a local computer device or created on a remote computer which is done by the aid of a certain software system or method through the means of a local computer, the user can then continue to create content that is stored locally and or on a remote computer or first get any content created on a local device or electronic gadget and get that data manually or automatically uploaded to a remote computer or server which again can be accessed later.

If a certain data is created on a local computer like device, a user also can access that information through another software application that aids in communicating with a local device through well-known commonly used networking technologies that connect computers to access data. If on the other hand, a user creates data on a remote computer through the use of the internet, a user can access that same information from any other computer that is connected to the same remote computer on which the user's data or information is stored. In the case of smart phones and similar devices, a user can manually create a user account or profile on that device and gain access to that same device through various authentication systems like a password method or other biometric sensors to more easily log in to that particular device. These smart devices and many other computer systems have software applications when enabled can back up or store a device's user profile and selected data to a remote computer.

When a user may want to access the backed-up information on a different device, that user must first be able to access his or her respective account through that device and manually get the data to download to that particular device if such device is able to download it. Therefore, even though there are many automatic functions that may be taking place on a computer like device, one thing that is always required is the manual creation of a user profile and a manual enablement of a backup feature to store user created content remotely and a manual action taken by a user to retrieve a specified type of data on to any similar or dissimilar device if such is possible.

In all these situations, a manually created user profile is most often associated with a very particular hardware or software function that can be stored remotely and that which can be retrieved manually to any particular device if such a device is capable of retrieving it and downloading and installing it for further use by a user. Also, currently, a single auto generated or auto created user profile is never associated with intelligently and automatically storing multiple disparate devices' information which further can be automatically and intelligently accessed and downloaded for further automatic installation and use by any other device from a central computer server.

In light of above-mentioned problems, it is desirable to provide a software system that can automatically create personal or an individual profile based on a number of biometric sensors in the first instance and in the second instance, automatically gather and save a local device's configuration information along with user generated or created information on that local device and in the third instance, automatically upload both the automatically created user profile and the local device's information and the user generated data or information. This automatic creation and uploading of user data and device data along with any user created data can also take place on any number of similar or dissimilar devices and get all of that data stored on a remote computer under the same single user profile which then can be accessed on any device which may have that capability to retrieve a user's profile and device information through biometric or other authentication methods to more easily aid the use of any kind of computer or smart device to accomplish various tasks thus saving time and efforts by a user who might otherwise is required to manually upload and download a personal profile and associated device settings and user created data for further use.

SUMMARY OF THE INNOVATION

The present invention discloses a highly automated computer software operating system that enables the automatic creation of one or more personal profile accounts based on a number of biometric sensors, and the automatic detection and storing of a local device's information and any user generated information or data, with all this data or information automatically uploaded and saved under the same individual profile account on a remote computer with the ability to store many different types of device information and its associated user created information. This automatic method and loop of creating and storing and updating personal and various device information or data in one place under the same user profile also enables the easy retrieval of that same information for automatic access and usage on any capable device and end terminal with biometric authentication methods thus enabling infinite possibilities for a user to more easily be more productive in creating and accessing user generated content from anywhere or any device with minimal manual input or activity.

In one embodiment, the system is configured to automatically create an individual profile or multiple profiles based on the presence and interaction of multi-factor biometric sensors of a user device/hardware device or multi-factor biometric authentication system that could be a combination of hardware and software in nature that further works with onboard storage, memory and networking modules among other features to enable all the current features as described above to be executed. In one embodiment, the onboard biometric sensors have the ability to test a blood sample, detect a fingerprint mark, a contactless finger print method of detection, a facial detection, iris detection, and even through a password method of creating a user profile.

In one embodiment, the system is configured to automatically generate user profiles for individuals. In one embodiment, the system comprises a computing device having a processor and a memory having a software module executed by the processor, wherein the software module is at least one of a plugin component and/or a browser extension. In one embodiment, the processor is in communication with a server via a network and configured to execute a set of instructions stored in the memory. In one embodiment, a database in communication with the server is configured to store data related to user's profile, wherein the database comprises one or more program modules, which are executed by the processor to perform multiple operations to include, but not limited to, creating a plurality of user profiles or personal accounts through the use of onboard biometric sensors on a hardware device or user device or a multi-factor biometric authentication system, generating passwords automatically associated with the plurality of user profiles or personal accounts when the user profiles are successfully completed by the help of a multi-factor biometric authentication system on board the user device or hardware device, thereby enabling the user to log in automatically by mere presence or exposure to the biometric authentication systems into the system to access the user profile or personal account using the user device. In one embodiment, the user device is at least any one of, but not limited to, a computer, a laptop, a smartphone, a personal digital assistant (PDA), a tablet, a credit card terminal, a point of sale terminal (POS), an entertainment device or TV, a medical terminal, and a travel terminal. The network mechanism to connect to and through is at least any one of, but not limited to, Wi-Fi, Bluetooth®, wireless local area network (WLAN)/Internet connection, and radio communication.

In one embodiment, the system is further configured to upload and download data and information related to auto created user profile from the server unless user manually stops. In one embodiment, the created user profile includes, but not limited to, images of the user, voice, touch-based biometric, an iris recognition (using the rear or front-facing camera), finger prints by touch or no touch on a designated area, a retinal scan, DNA sample, a palm print, a hand geometry, odor/scent, and gait. In one embodiment, the computing device is at least any one of a computer, a laptop, a smartphone, a personal digital assistant (PDA), and a tablet.

In one embodiment, the system could allow the users to change the auto generated passwords associated with the user profile or personal account. In one embodiment, the system could enable the user to automatically log in or log out based on presence or absence to the associated user profile or personal account on that user device as needed from time to time. In one embodiment, the system is further configured to detect and store the user device's information in association with or along with the auto created user profile. In one embodiment, the system is further configured to automatically categorize the generated information or data associated with the created user profile on the computing device. In one embodiment, the system is further configured to automatically store the user generated information or data associated with the created user profiles from multiple devices through the use of networking technologies, memory, and server and/or storage modules of the computing device remotely like on a cloud. In one embodiment, the system is further configured to automatically download any user profile from a server to any other computing device for further use on that local device. In one embodiment, the system is further configured to continuously upload and download to and from the server in an infinite loop unless a user manually stops such auto created information related to the user, user device, and the data created by the user. In one embodiment, the system is further configured to enable the user to check all the user devices and its associated data or information stored on the server and/or a computing device on a local device, thereby making it possible for the stored data or information to be of further use by the user.

Other objects, features and advantages of the present innovation will become apparent from the following detailed description. It should be understood, however, that the detailed description and the specific examples, while indicating specific embodiments of the innovation, are given by way of illustration only, since various changes and modifications within the spirit and scope of the innovation will become apparent to those skilled in the art from this detailed description.

BRIEF DESCRIPTION OF DRAWINGS

The foregoing summary, as well as the following detailed description of the innovation, is better understood when read in conjunction with the appended drawings. For the purpose of illustrating the innovation, exemplary constructions of the innovation are shown in the drawings. However, the innovation is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

A description of embodiments of the present innovation will now be given with reference to the Figures. It is expected that the present innovation may be embodied in other specific forms without departing from its spirit or essential characteristics. The described embodiments are to be considered in all respects only as illustrative and not restrictive.

Figure 1:
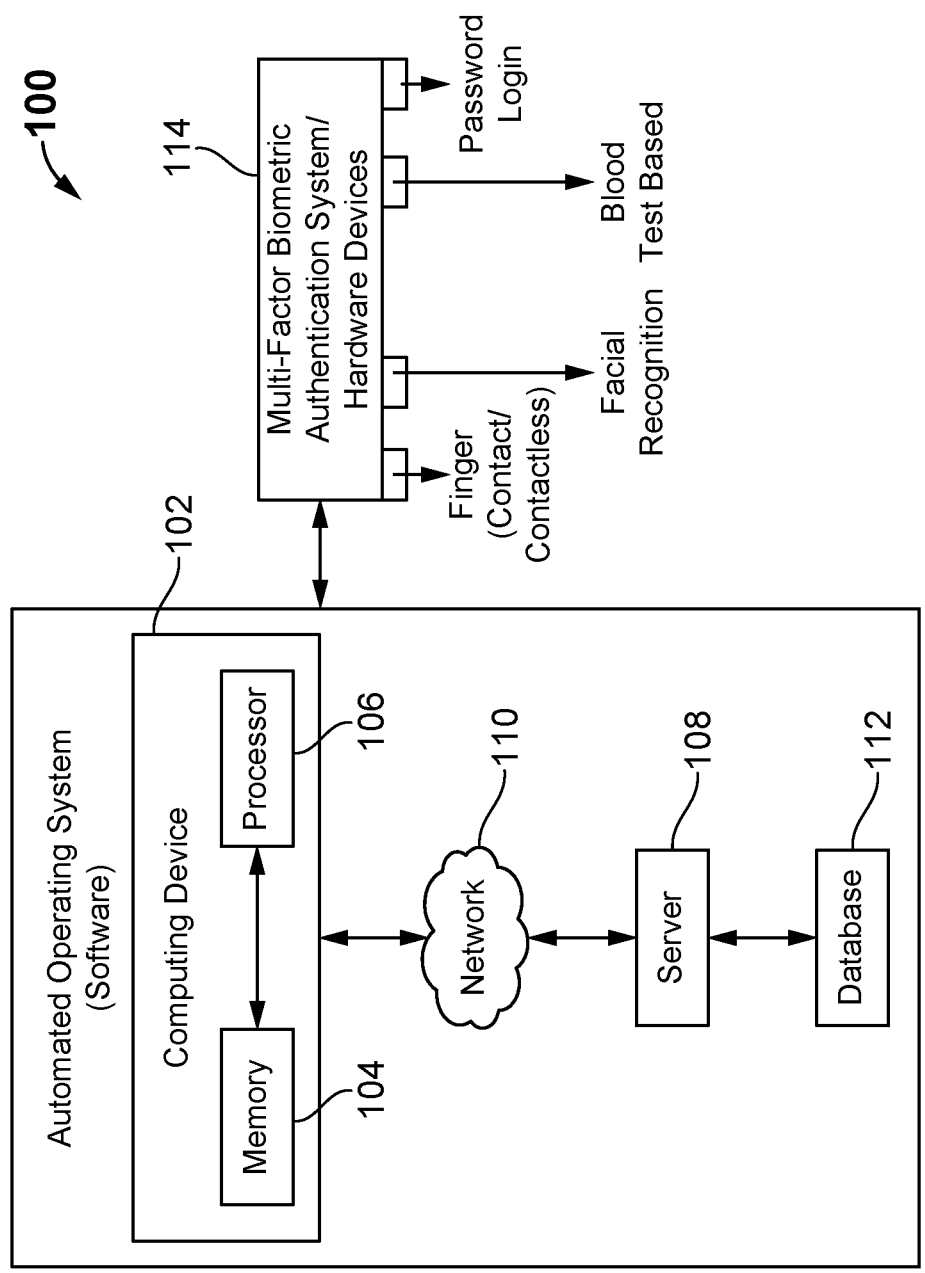
FIG. 1 shows a view of an automated computer software operating system's auto profile creation module or algorithm with the aid of multi-factor biometric authentication sensors, according to one embodiment of the present invention.

Referring to FIG. 1, an automated computer software operating system 100 in one embodiment is disclosed. In one embodiment, the system 100 is configured to automatically create an individual profile or multiple profiles based on the presence and interaction of multi-factor biometric sensors of a user device/hardware device or multi-factor biometric authentication system 114 that could be a combination of hardware and software in nature that further works with onboard storage, memory and networking modules among other features to enable all the current features as described above to be executed. In one embodiment, the onboard biometric sensors have the ability to test a blood sample, detect a fingerprint mark, a contactless finger print method of detection, a facial detection, an iris detection, and even through a password method of creating a user profile.

In one embodiment, the system 100 is configured to automatically generate user profiles for individuals. In one embodiment, the system 100 comprises a computing device 102 having a processor 106 and a memory 104 having a software module executed by the processor 106, wherein the software module is at least one of a plugin component and/or a browser extension. In one embodiment, the processor 106 is in communication with a server 108 via a network 110 and configured to execute a set of instructions stored in the memory 104. In one embodiment, a database 112 in communication with the server 108 is configured to store data related user's profile, wherein the database 112 comprises one or more program modules, which are executed by the processor 106 to perform multiple operations include, but not limited to, creating a plurality of user profiles or personal accounts through the use of onboard biometric sensors on a hardware device or user device or a multi-factor biometric authentication system 114, generating passwords automatically associated with the plurality of user profiles or personal accounts when the user profiles are successfully completed by a multi-factor biometric authentication system 114 on board the user device or hardware device, thereby enabling the user to login into log in to the system 100 to access the user profile or personal account using the user device. In one embodiment, the user device is at least any one of, but not limited to, a computer, a laptop, a smartphone, a personal digital assistant (PDA), a tablet, a credit card terminal, a point of sale terminal (POS), an entertainment device or TV, a medical terminal, and a travel terminal. The network 110 is at least any one of, but not limited to, Wi-Fi, Bluetooth®, wireless local area network (WLAN)/Internet connection, and radio communication.

In one embodiment, the system 100 is further configured to upload and download data and information related to an auto created user profile from the server unless user manually stops. In one embodiment, the created user profile includes, but not limited to, images of the user, voice, touch-based biometric, an iris recognition (using the rear or front-facing camera), finger prints, a retinal scan, DNA sample, a palm print, a hand geometry, odor/scent, and gait. In one embodiment, the computing device 102 is at least any one of a computer, a laptop, a smartphone, a personal digital assistant (PDA), and a tablet.

In one embodiment, the system 100 could allow the users to change the auto generated passwords associated with the user profile or personal account. In one embodiment, the system 100 could enable the user to automatically log in or log out based on presence or absence to the associated user profile or personal account on that user device as needed from time to time. In one embodiment, the system 100 is further configured to detect and store the user device's information in association with or along with the auto created user profile. In one embodiment, the system 100 is further configured to automatically categorize the generated information or data associated with the created user profile on the computing device 102. In one embodiment, the system 100 is further configured to automatically store the user generated information or data associated with the created user profiles from multiple devices through the use of networking technologies, memory, and server and/or storage modules of the computing device remotely. In one embodiment, the system 100 is further configured to automatically download any user profile from the server 108 to any other computing device for further use on that local device. In one embodiment, the system 100 is further configured to continuously upload and download to and from the server 108 in an infinite loop unless a user manually stops such auto created information related to the user, user device, and the data created by the user. In one embodiment, the system 100 is further configured to enable the user to check the user device and its associated data or information stored on the server 108 and/or the computing device on any local device 102, thereby using the stored data or information for further use by the user.

Figure 2:
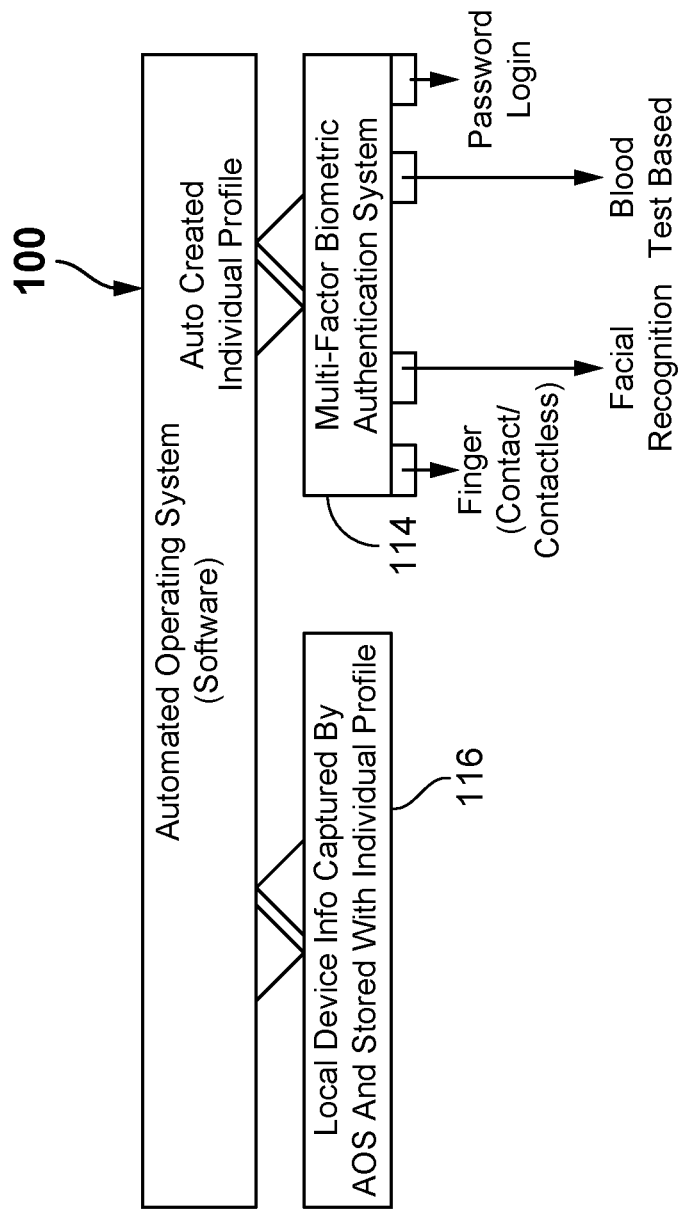
FIG. 2 shows a view of an automated computer software operating system's ability to detect and store a local device's unique information under the auto created profile account, according to one embodiment of the present invention.

Referring to FIG. 2, a block diagram of the system 100 configured to automatically detect the features and configuration of the local device in one embodiment is disclosed. In one embodiment, the system 100 is configured to be able to automatically detect the features and configuration of that local device and install itself on it as required for further use 116 and save that same information along with the auto created user profile onboard that local device. The local device information is captured by the automated operating system (AOS) and stored with the individual profiles.

Figure 3:
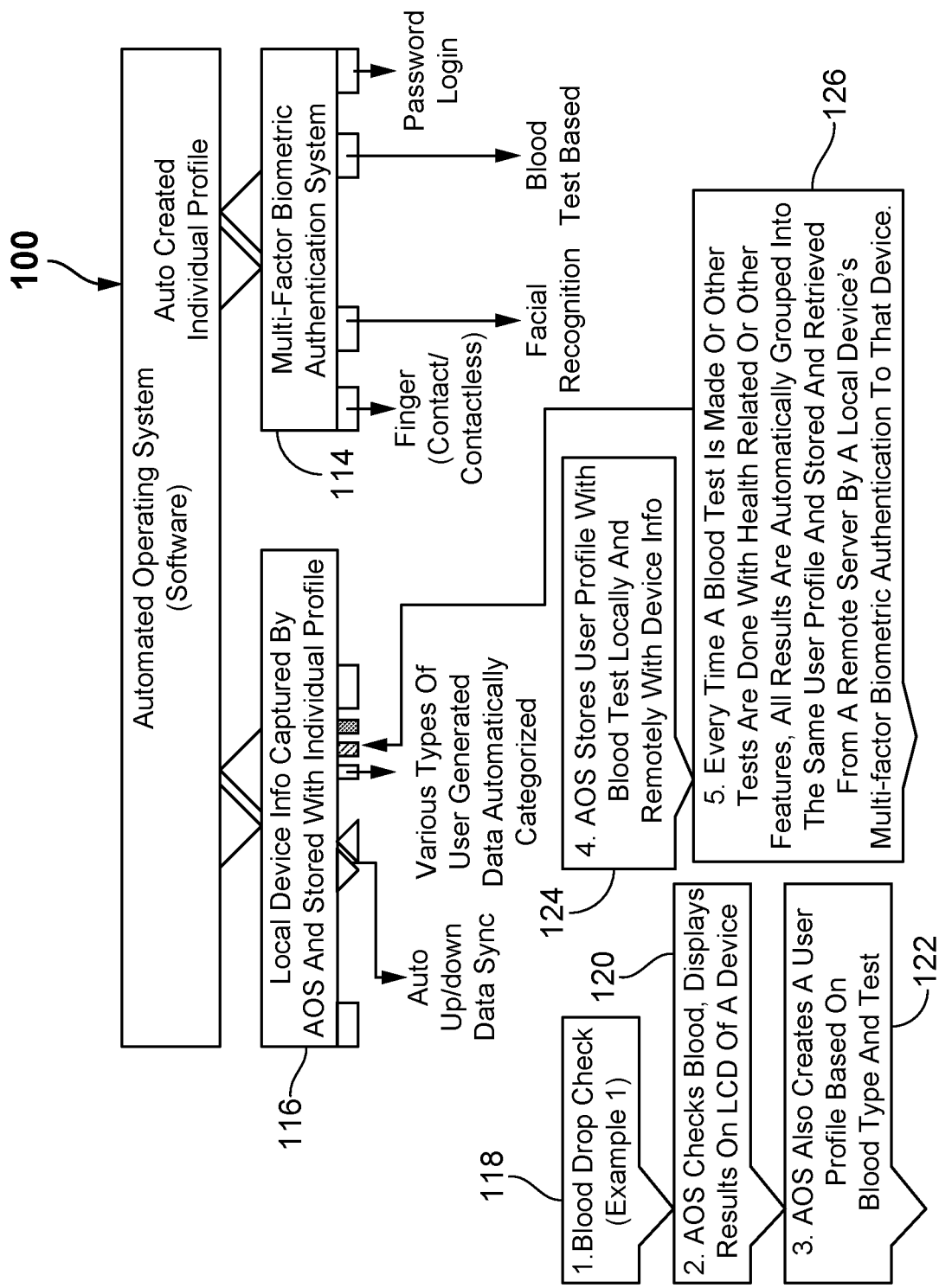
FIG. 3 shows a view of an automated computer software operating system's ability to auto categorize all the user generated or created data in the auto created profile of each user, according to one embodiment of the present invention.

Referring to FIG. 3, a block diagram of the system 100 configured to automatically categorize the generated information or data associated with the created user profile on the computing device 102 in one embodiment is disclosed. In one embodiment, the system 100 is able to enable the user to create or generate new data based on the features of the local device and this information is automatically categorized by its type in various categories and saved under the same auto created user profile of this present invention. In an exemplary embodiment, at one step 118, the onboard biometric sensors on the hardware device or multi-factor biometric authentication system 114 could be able to test and check a blood drop. At other steps 120 and 122, the AOS checks the blood and displays the results on the screen (LCD) of the device and also creates the user profile based on the blood type and test. Further, at another step 124, the AOS stores the created user profile with the blood test locally and remotely with the device information. Further at another step 126, every time a blood test is made or other tests are done with health related or other features, all results are automatically grouped into the same user profile and stored and retrieved from the server 108 or a remote server by a local device's multi-factor biometric authentication system 114 of the hardware device, for example, a computer or a laptop.

Figure 4:
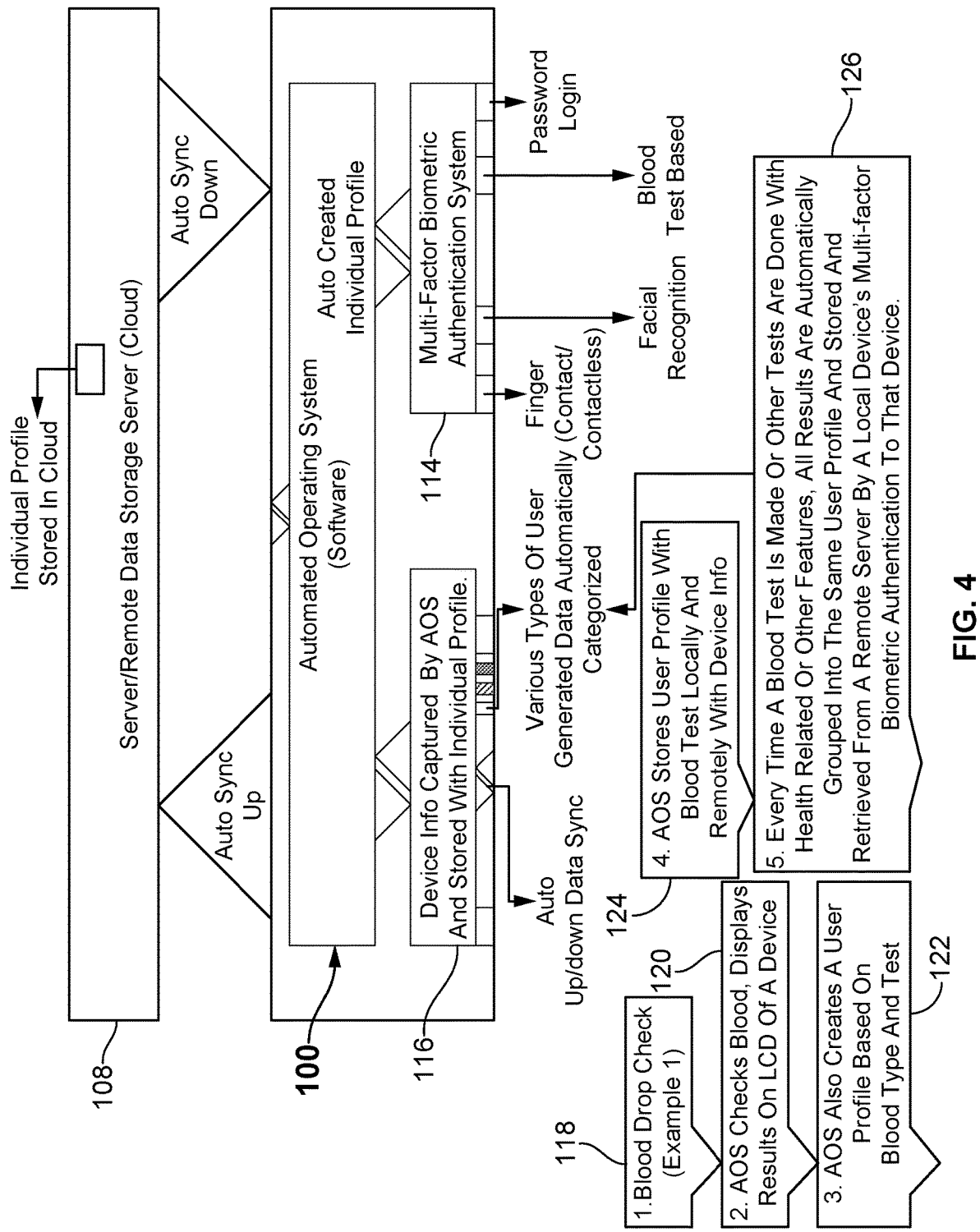
FIG. 4 shows a view of an automated computer software operating system's ability to store in an auto created database all the auto created profile(s), device(s) information, and user generated data information on a remote computer or server through the aid of any networking technologies, according to one embodiment of the present invention.
Figure 5A:
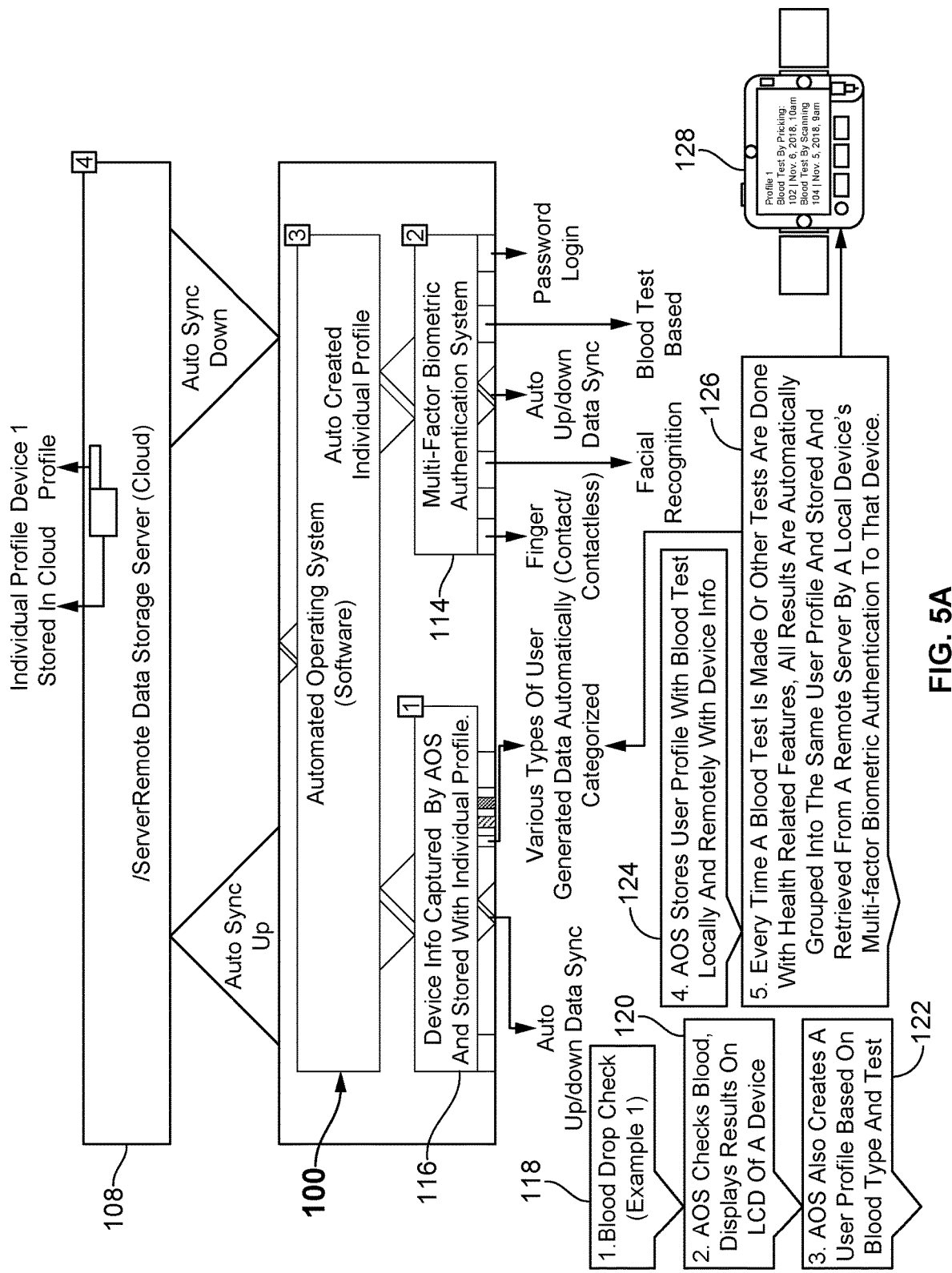
FIGS. 5A-5G shows a view of an automated computer software operating system's ability to automatically retrieve or download any centrally stored information that was auto created on to any other local device for further use as the local device may enable without the need for many manual operations, according to one embodiment of the present invention.
Figure 5B:
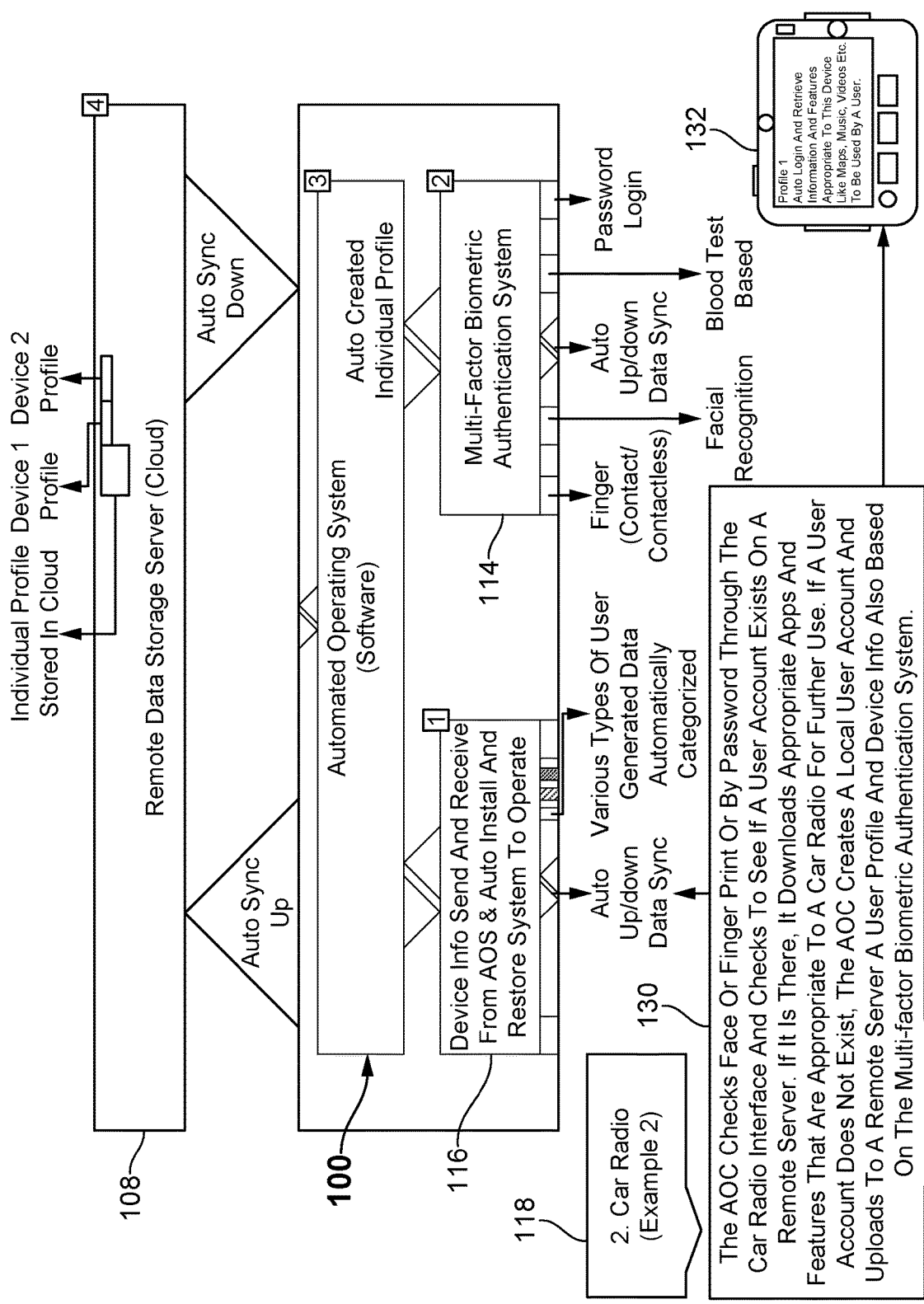
Figure 5C:
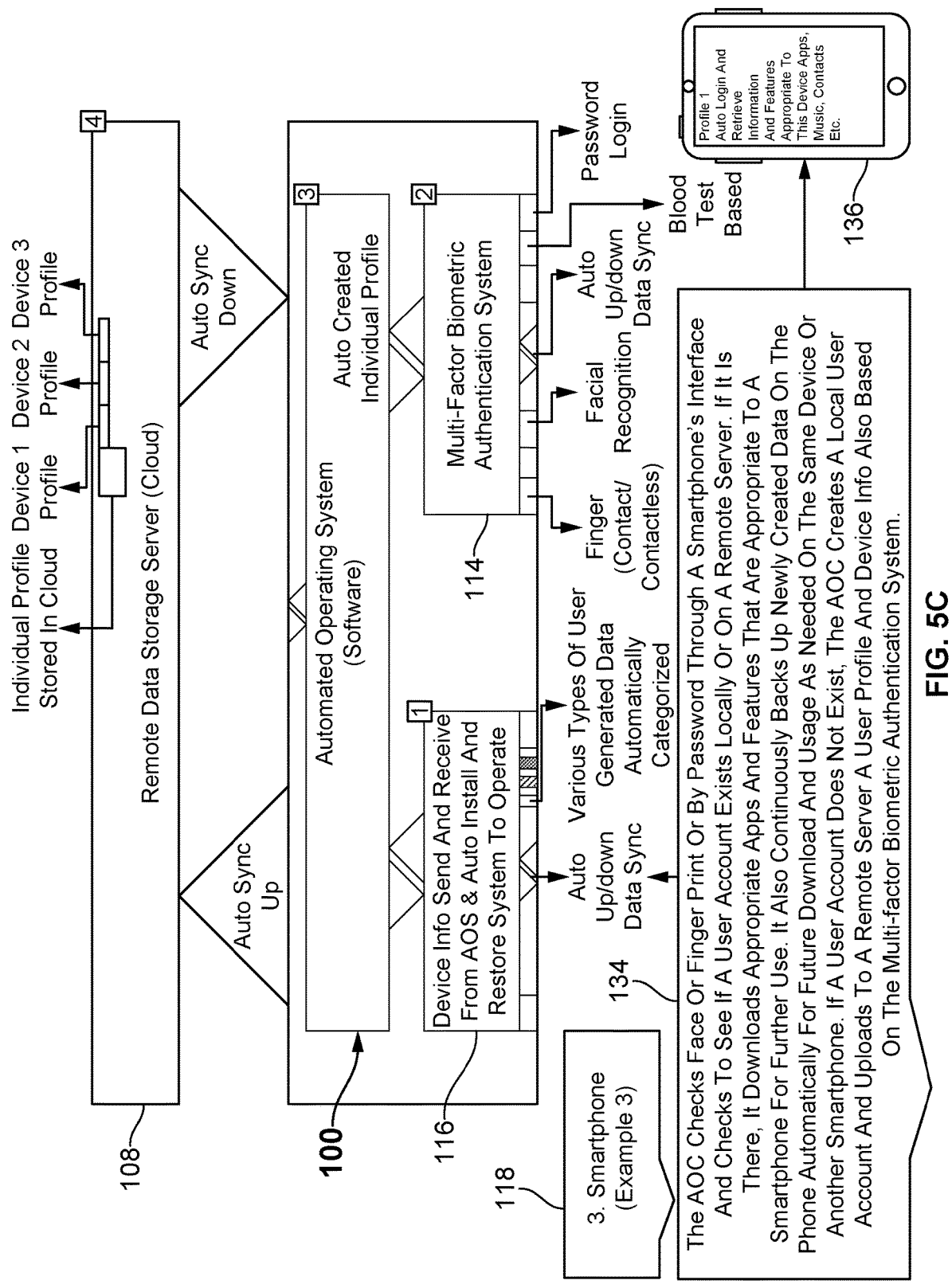
Figure 5D:
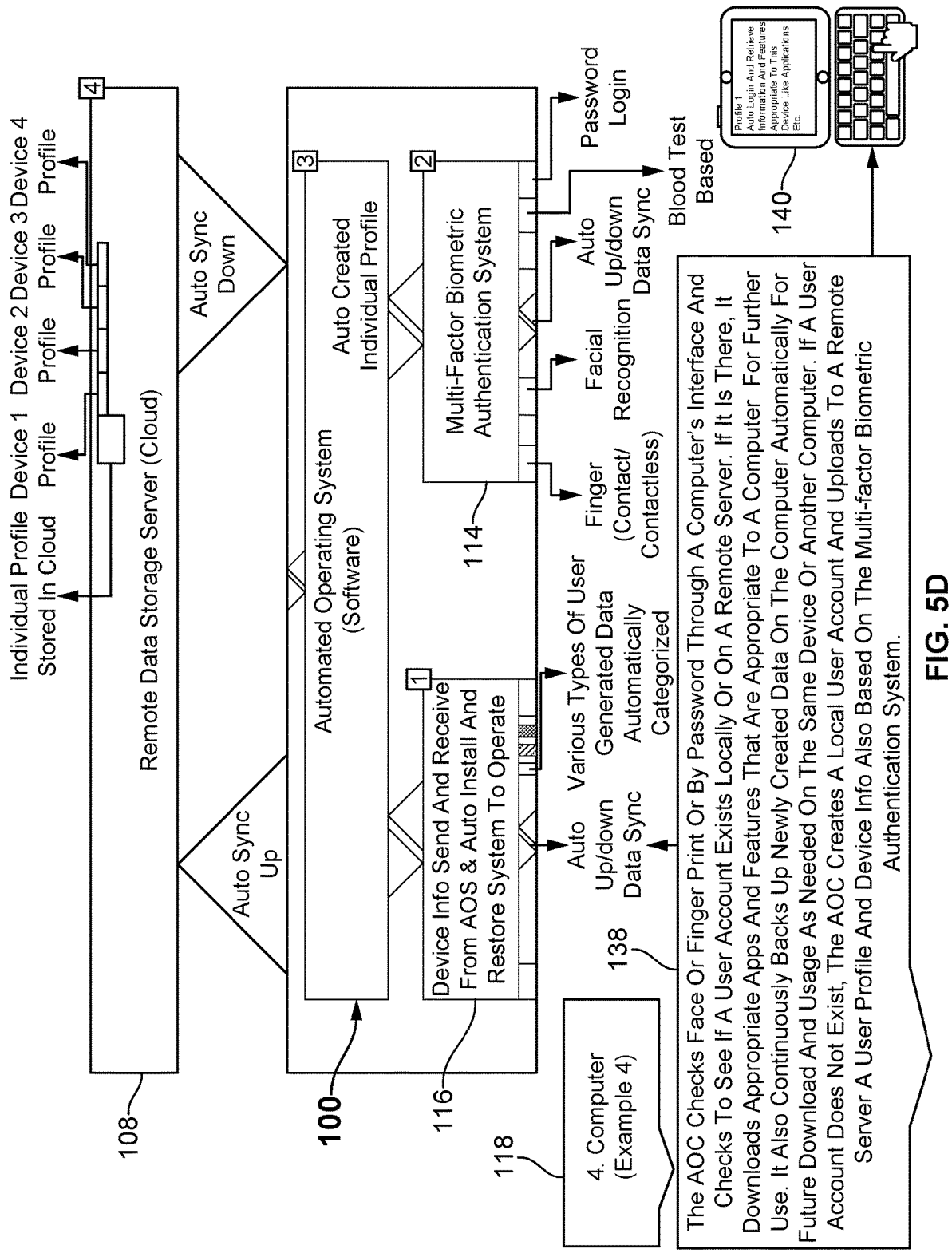
Figure 5E:
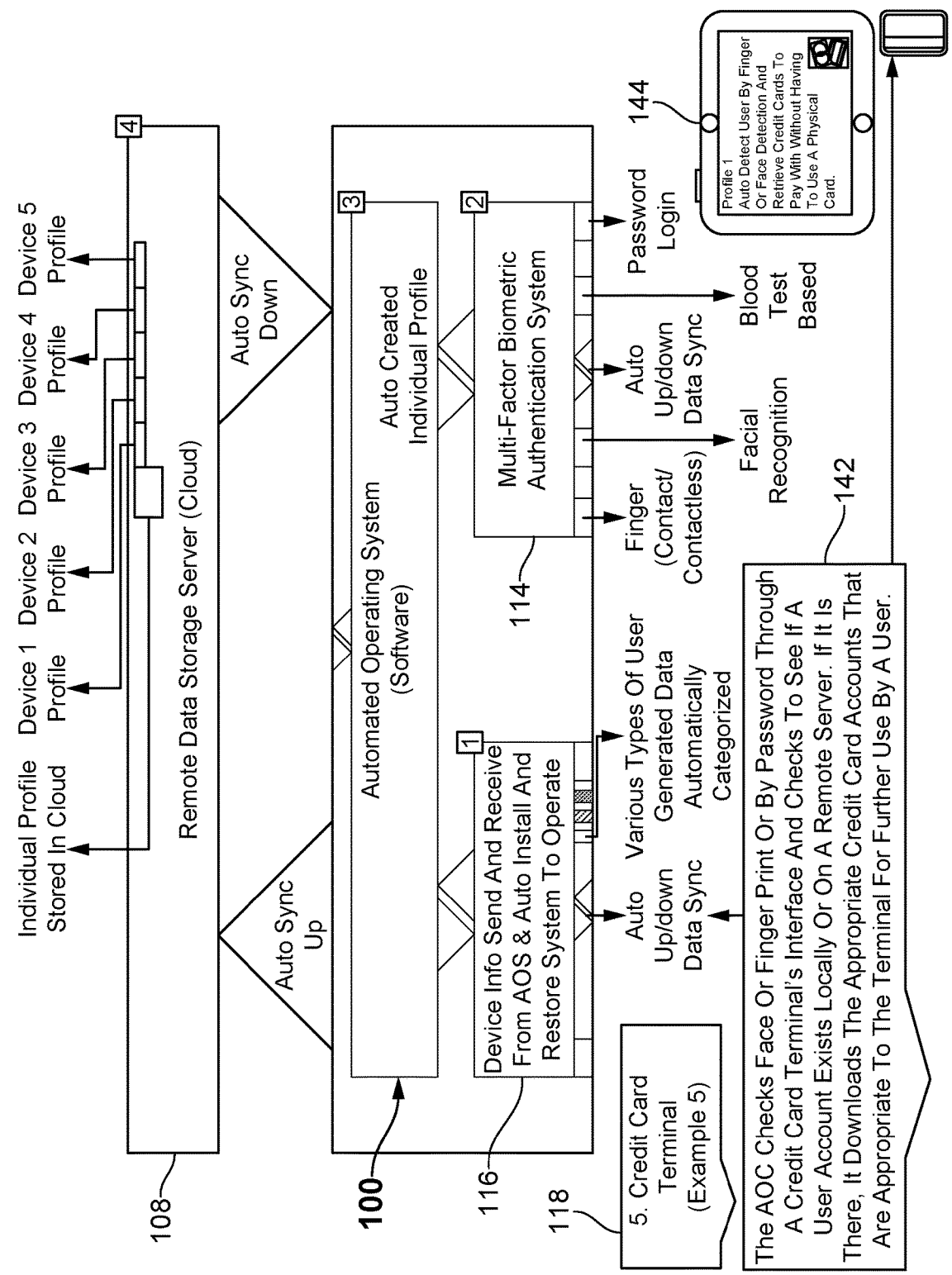
Figure 5F:
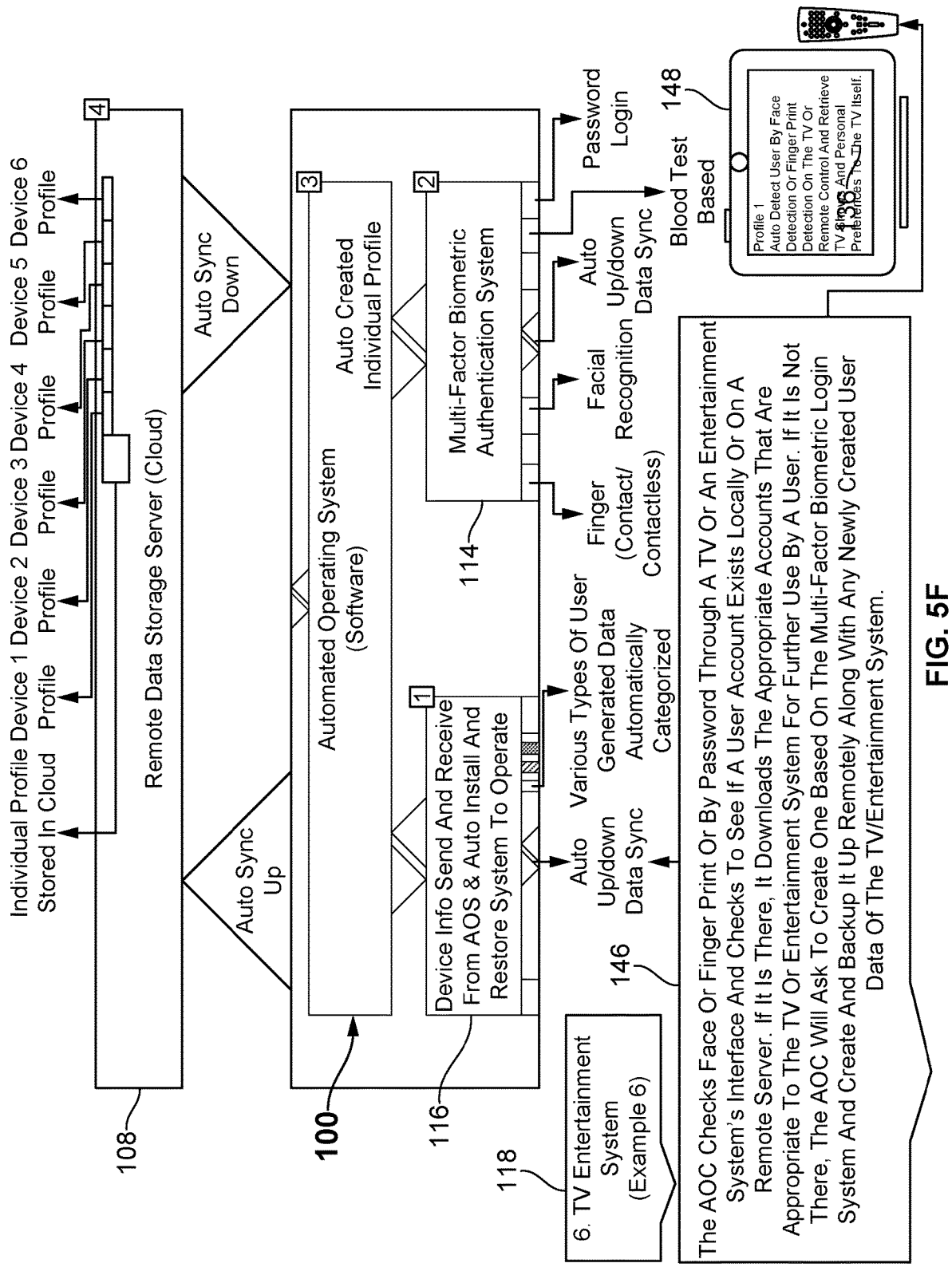
Figure 5G:
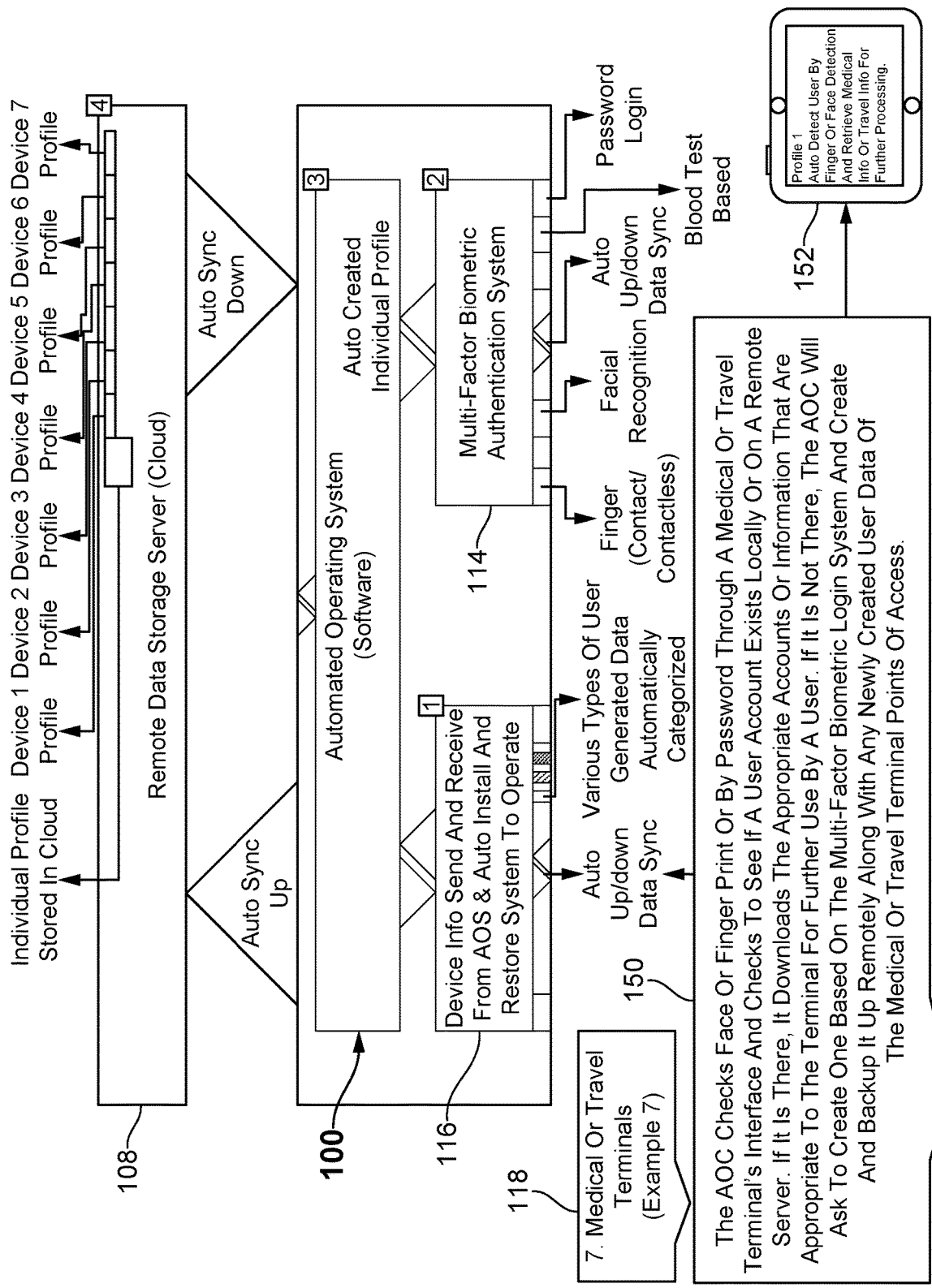

Referring to FIG. 4, the block diagram of the system 100 configured to automatically transmit the data created on the local device to the server or remote data storage server 108 in one embodiment is disclosed. In one embodiment, the system 100 is configured to automatically transmit the data created on the local device to the server or remote data storage server (cloud) 108 via the network, for example, a wireless communication or a wired communication and with such feature on the local device itself and store it automatically under the uniquely created user profile on the local device but also on the remote computer or server 108.

Referring to FIGS. 5A-5G, a block diagram of the system 100 configured to automatically save unlimited amounts of devices' information and their associated user generated information under the same unique user profiles that were created automatically on the local device through the aid of multifactor biometric sensors in one embodiment is disclosed. In one embodiment, the system 100 could automatically save unlimited amounts of devices' information and their associated user generated information under the same unique user profiles that were created automatically on the local device through the aid of multifactor biometric sensors. In an exemplary embodiment, the system 100 could use blood samples for automatically creating the user profile. In an exemplary embodiment, the blood test results could display on the screen (LCD) of the device 128, for example, a blood test apparatus. The system 100 further creates the user profile based on the blood type and test.

In yet another exemplary embodiment, the system 100 could use a car radio interface 132 for checking face or finger prints or by password for automatically creating the user profile. In one embodiment, at step 130, the AOS could check face or finger prints or by password through the car radio interface 132 and check if the user account exists on the server 108 or a remote server (cloud). If the user account exists then it downloads the appropriate apps and features that are appropriate to the car radio interface for further use. If the user account does not exist then the AOS creates a local user account and uploads to the server 108 or remote server and also uploads the user profile and device information based on the multi-factor biometric authentication system 114. In an exemplary embodiment, the features and apps could be displayed on the screen of the car radio interface 132, for example, a blood test apparatus.

In yet another exemplary embodiment, the system 100 can check face or a finger print or by a password entry through a smartphone's interface 136 for automatically creating a user profile. In one embodiment, at step 134, the AOS can check face or finger print or by password through the smartphone's interface 136 and checks if a user account exists locally or on the server or a remote server 108. If the account already exists then it downloads appropriate apps and features that are appropriate to the smartphone 136 for further use. It also continuously backs up newly created data on the smartphone 136 automatically for future download and usage as needed on the same device or another smartphone. If the user account does not exist then the AOS creates a local user account and uploads to the server or a remote server 108 and also uploads the user profile and device information based on the multi-factor biometric authentication system automatically 114. In an exemplary embodiment, the features and apps could be displayed on the screen of the smartphone 136.

In yet another embodiment, the system 100 could check face or finger print or by password through a computer's interface 140 for automatically creating the user profile. In one embodiment, at step 138, the AOS could check face or finger print or by password through a computer's interface 140 and checks if a user account exists locally or on the server or a remote server 108. If the user account already exists then it downloads appropriate apps and features that are appropriate to the computer 140 for further use. It also continuously backs up newly created data on the computer 140 automatically for future download and usage as needed on the same device or another device or computer. If the user account does not exist, the AOS creates a local user account and uploads to the server or a remote server 108 and also uploads the user profile and device information based on the multi-factor biometric authentication system 114. In an exemplary embodiment, the features and apps could be displayed on the screen of the computer or device 140.

In yet another embodiment, the system 100 could check face or finger print or by password through a credit card terminal's interface 144 for automatically creating the user profile. In one embodiment, at step 138, the AOS could check face or finger print or by password through the credit card terminal's interface 144 and checks if a user account exists locally or on the server or a remote server 108. If it is there, it downloads the appropriate credit card accounts that are appropriate to the terminal for further use by the user.

In yet another embodiment, the system 100 could check face or finger print or by password through a television (TV) or an entertainment system's interface 148 for automatically creating the user profile. In one embodiment, at step 146, the AOS can check face or finger print or by password through the television (TV) or entertainment system's interface 148 and checks if a user profile or account exists locally or on the server or a remote server 108. If it is there, it downloads the appropriate accounts that are appropriate to the TV or Entertainment system for further use by the user. If the user profile or account does not exist then the AOS will ask to create a user profile based on the multi-factor biometric log in system 114 and create and backup it up remotely along with any newly created user data of the TV/Entertainment system.

Figure 6:
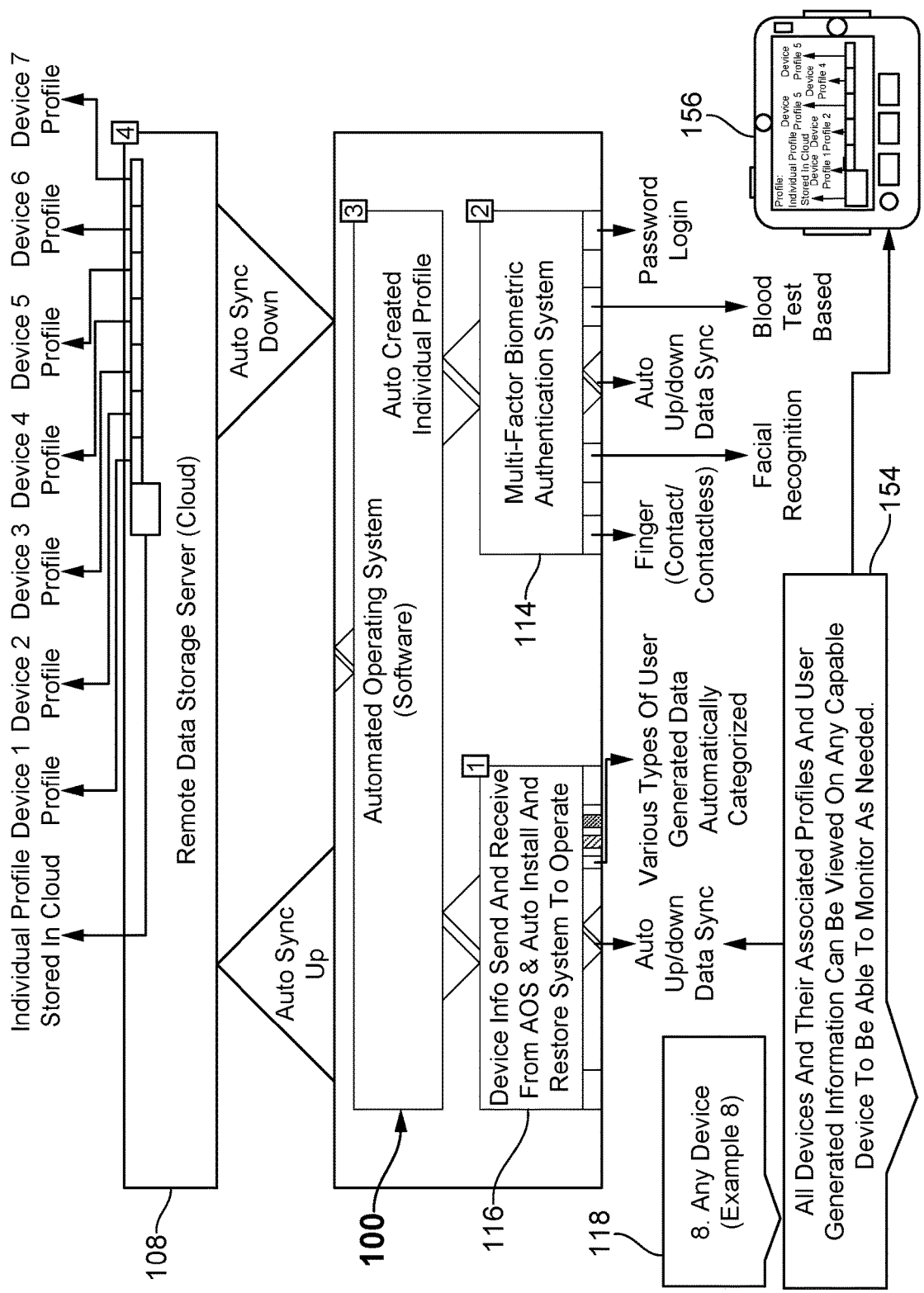
FIG. 6 shows a view of an automated computer software operating system's ability to automatically download and show the information of all the various devices stored on a remote computer for monitoring purposes if such is enabled by a local device or computer, according to one embodiment of the present invention.

Referring to FIG. 6, the system 100 is configured to automatically download auto-created and remotely stored user profile(s) and its associated device information and associated user generated or created data or information in one embodiment is disclosed. In one embodiment, the system 100 is configured to automatically download auto-created and remotely stored user profile(s) and its associated device information and associated user generated or created data or information from a remote computer server 108 to any other local device 156 to that local device through the means of onboard modules that consist of networking features, memory and storage modules for further use by any user. This process of biometric based automatic downloading and uploading of user profiles and associated device data and user created data always continues in an infinite loop unless manually stopped by the user with a feature to enable such. At step 154, all devices and their associated profiles and user generated information can be viewed on any capable device 156 to be able to monitor as needed.

Figure 7:
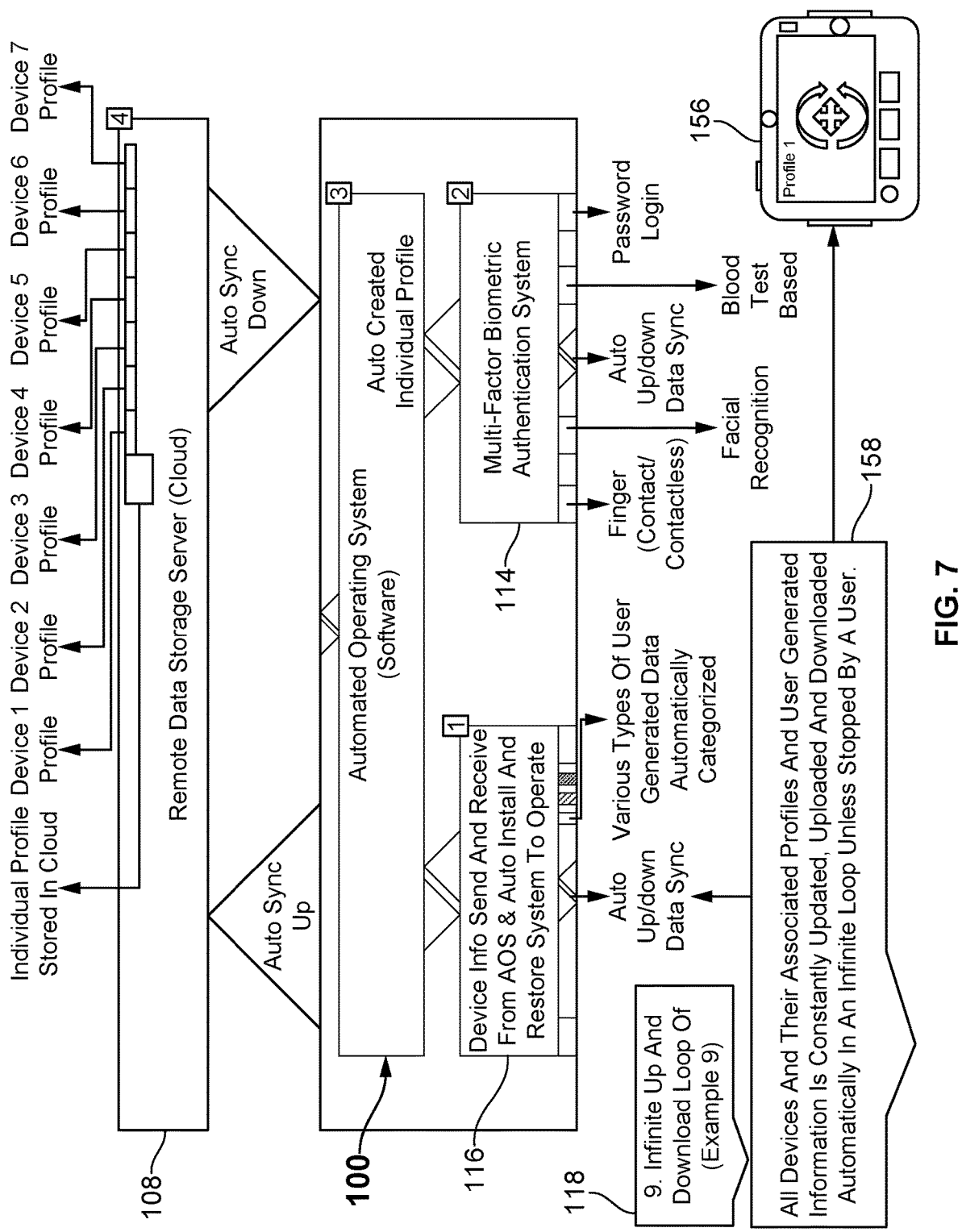
FIG. 7 shows a view of an automated computer software operating system's ability to retrieve all the information of various devices stored under an auto generated user profile to display on any capable device for simple viewing.

Referring to FIG. 7, the system 100 is configured to automatically download the auto-created and remotely stored user profile(s) and its associated device information and associated user generated or created data or information through the means of onboard modules in one embodiment is disclosed. In one embodiment, the system 100 is configured to automatically download the created and remotely stored user profile(s) and its associated device information and associated user generated or created data or information from a remote computer server 108 to any another local device 156 to that local device through the means of onboard modules that consist of networking features, memory and storage modules for further use by any user. At step 158, all devices and their associated profiles and user generated information is constantly updated, uploaded and downloaded automatically in an infinite loop unless stopped by the user.

Preferred embodiments of this innovation are described herein, including the best mode known to the inventors for carrying out the innovation. It should be understood that the illustrated embodiments are exemplary only and should not be taken as limiting the scope of the innovation.

The foregoing descriptions comprise illustrative embodiments of the present innovation. Having thus described exemplary embodiments of the present innovation, it should be noted by those skilled in the art that the disclosures are exemplary only, and that various other alternatives, adaptations, and modifications may be made within the scope of the present innovation. Merely listing or numbering the steps of a method in a certain order does not constitute any limitation on the order of the steps of that method. Many modifications and other embodiments of the innovation will come to mind to one skilled in the art to which this innovation pertains having the benefit of the teachings in the foregoing descriptions. Although specific terms may be employed herein, they are used only in a generic and descriptive sense and not for purposes of any limitations. Accordingly, the present innovation is not limited to the specific embodiments illustrated herein.

What is claimed is:

1. An automated operating system for automatically generating profiles for individuals, comprising,
  a computing device that comprises a processor and a memory feature and having a software module executed by the processor, wherein the software module is at least one of a plugin component and/or a browser extension,
  wherein the processor is in communication with a server via a network and configured to execute a set of instructions stored in the memory;
  a database in communication with the server configured to store data related to a user's profile, wherein the database comprising one or more program modules, which are executed by the processor to perform multiple operations, comprising:
    creating a plurality of user profiles or personal accounts and automatically save unlimited amounts of computing device information and their associated user generated information under the same unique user profiles that were created automatically through the use and interaction of a sensory group consisting of onboard biometric sensors on a hardware device or user device or a multi-factor biometric authentication system, wherein the onboard biometric sensors are configured to test a blood sample, detect a fingerprint mark, a contactless finger print method of detection, a facial detection, an iris detection, and wherein one or more detected biometric information is sent to an analysis module and said database, thereby the detected biometric information is compared with an existing database in the analysis module to check whether the user's profile and respective login information are already exists in the first instance, and if any one of detected biometric information of a user found to be not available, then a new user profile is automatically created and stored in any one of the analysis module or the database and enables automatic generation of password thereby enabling the user to login and use a particular type of computing device; wherein, any one of content created or generated or changed in the particular type of computing device is automatically sent to the automated operating system, stored and updated constantly in a loop like operation without any intervention of the user;
  if a user profile already exists after any of the biometric-based sensors detect any such user by the comparison method in the analysis module or database located in the automated operating system, then the user is automatically allowed to log in to any particular hardware or device installed with automated operating system for further use of the particular device, thereby whatever information is interacted and created by the use of any installed software on that particular device is once again sent to the automated operating system and stored and constantly updated in a loop like operation without the intervention of a user thereby enabling the user in ease to access any device from anywhere;
  wherein the user's information is first collected by the onboard biometric sensors or the sensory group installed on any device is utilized by the analysis module residing on the server of the automated operating system to create and authenticate a user profile, and each uniquely created user profile consists images of the user, voice, touch-based biometric, an iris recognition (using any one of rear or front-facing camera), finger prints, a retinal scan, DNA sample, a palm print, a hand geometry, odor/scent, and gait;
  generating passwords automatically associated with the plurality of user profiles related to any number of unique devices and unique respective profiles to automatically log in and use respective devices without any manual input of a user;
  wherein the users further can change the auto generated passwords associated with his or her user profile or personal account if such maybe desired for manual login by a textual password input method;
  thereby the automated operating system enable a user to automatically log in or log out based on mere presence or absence to the visible proximity of any hardware device from anywhere using the auto-created user profile or personal account based on any hardware device and its profile by the use of the multi-factor biometric authentication system in tandem with the analysis module of the automated operating system as needed from time to time;

any number or different users can use the same hardware device(s) by being automatically logged into those devices by the multi-factor biometric authentication method of the automated operating system that has the aforesaid analysis module or database of all user records saved centrally and thereby also not only get logged into the respective or same hardware devices to be used but also to automatically get or retrieve the content that may have been already saved of each hardware profile in each respective user's account and its corresponding content, then retrieved automatically to that particular hardware device and even auto configured to it if such maybe needed for a user to start using it, if the hardware device allows it, a user can also preview in a thumbnail like representation all the various hardware profiles saved in the user's account centrally in one section or window on that particular hardware device the user may have logged automatically into.

2. The system of claim 1, is further configured to upload and download data and information related to an auto created profile from the server unless a user manually stops.

3. The system of claim 1, wherein the computing device is at least any one of a computer, a laptop, a smartphone, a personal digital assistant (PDA), and a tablet, wherein the hardware device or user device is at least any one of a computer, a laptop, a smartphone, a personal digital assistant (PDA), a tablet, a credit card terminal, a point of sale terminal (POS), an entertainment device or TV, a medical terminal, and a travel terminal.

4. The system of claim 1, is further configured to detect and store the user device's information in association with or along with the auto created plurality of user profiles or personal accounts.

5. The system of claim 1, is further configured to automatically categorize one or more generated information or data associated with the created plurality of user profiles or personal accounts on the computing device.

6. The system of claim 1, wherein the network is at least any one of Wi-Fi, Bluetooth®, wireless local area network (WLAN)/Internet connection, and radio communication.

7. The system of claim 1, is further configured to automatically store the one or more user generated information or, data associated with the created plurality of user profiles or personal accounts from multiple devices through the use of networking technologies, memory, and server and/or storage modules of the computing device remotely.

8. The system of claim 1, is further configured to automatically download any user profile and any associated device profiles along with any user created data or information that is associated with each profile and device from the server to any other computing device or gadget for further use on a local device by auto configuring itself to that local device according to the local device's parameters.

9. The system of claim 1, is further configured to continuously upload and download to and from the server in an infinite loop unless a user manually stops any one of an auto created information related to the user, hardware device or user device or the multi-factor biometric authentication system, and any one of a data created by the user.

10. The system of claim 1, is further configured to enable the user to check the hardware device or user device or the multi-factor biometric authentication system, and its associated data or information stored on the server and/or the computing device on any local device, thereby enabling the use of any one of a remotely stored data or information for further use by the user.

\* \* \* \* \*